US011001865B2

(12) United States Patent
Decker

(10) Patent No.: US 11,001,865 B2
(45) Date of Patent: May 11, 2021

(54) MODIFIED LECITHIN, PREPARATION THEREOF, AND USE AS AN ANTIOXIDANT

(71) Applicant: University of Massachusetts, Boston, MA (US)

(72) Inventor: Eric Decker, Sunderland, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 9 days.

(21) Appl. No.: 16/008,227

(22) Filed: Jun. 14, 2018

(65) Prior Publication Data

US 2018/0363015 A1    Dec. 20, 2018

Related U.S. Application Data

(60) Provisional application No. 62/612,796, filed on Jan. 2, 2018, provisional application No. 62/520,121, filed on Jun. 15, 2017.

(51) Int. Cl.
| | |
|---|---|
| *C11B 5/00* | (2006.01) |
| *C12P 13/06* | (2006.01) |
| *C12P 13/00* | (2006.01) |
| *C12P 7/64* | (2006.01) |

(52) U.S. Cl.
CPC .............. *C12P 13/06* (2013.01); *C11B 5/005* (2013.01); *C11B 5/0028* (2013.01); *C11B 5/0035* (2013.01); *C11B 5/0085* (2013.01); *C12P 7/6481* (2013.01); *C12P 13/001* (2013.01); *C12Y 114/13017* (2013.01); *C12Y 301/04004* (2013.01); *C12Y 114/1307* (2013.01)

(58) Field of Classification Search
None
See application file for complete search history.

(56) References Cited

U.S. PATENT DOCUMENTS

2002/0155558 A1* 10/2002 Kirschner ............ A61K 9/0014
                                                                435/128

OTHER PUBLICATIONS

Judde et al. "Antioxidant Effect of Soy Lecithins on Vegetable Oil Stability and Their Synergism with Tocopherols", JAOCS 80(12): 1209-1215 (Year: 2003).*
L. Kouriskima et al. "Phospholipids as Inhibitors of Oxidation During Food Storage and Frying", Prehrambeno-technol. biotechnol. rev. 32(2-3): 91-94. (Year: 1994).*
M. Kashima et al. "The Antioxidant Effects of Phospholipids on Perilla Oil", JAOCS 68(2): 119-122 (Year: 1991).*
Cardenia et al.; "Antioxidant and prooxidant activity behavior of phospholipids in stripped soybean oil-in-water emulsions"; J Am Oil Chem Soc. 2011; 88(9):1409-1416.
Cui et al.; "Impact of phosphatidylethanolamine on the antioxidant activity of α-tocopherol and trolox in bulk oil"; Journal of agricultural and food chemistry. 2015; 63(12):3288.

(Continued)

*Primary Examiner* — Rebecca E Prouty
(74) *Attorney, Agent, or Firm* — Cantor Colburn LLP

(57) ABSTRACT

Disclosed are methods of making a modified lecithin by conducting an enzymatic conversion of a naturally derived lecithin to form a modified lecithin, e.g., having an enhanced level of phosphatidylethanolamine, phosphatidylserine, or a combination thereof. Compositions prepared from the modified lecithin and use to inhibit lipid oxidation are described.

7 Claims, 8 Drawing Sheets

(56) References Cited

OTHER PUBLICATIONS

Imamura, S. and Y. Horiuti, Enzymatic Determination of Phospholipase D Activity with Choline Oxidase. The Journal of Biochemistry, 1978. 83(3): p. 677-680.

Johnson et al.; "Development of iron-chelating poly(ethylene terephthalate) packaging for inhibiting lipid oxidation in oi-in-water emulsions"; Journal of agricultural and food chemistry. 2015; 63(20):5055.

Shantha et al.; "Rapid, Sensitive, Iron-Based Spectrophotometric Methods for Determination of Peroxide Values of Food Lipids"; Asoc of Anal Chem Int ; 77; pp. 421-424; (1994).

Yang, H. and M.F. Roberts; "Phosphohydrolase and transphosphatidylation reactions of two Streptomyces phospholipase D enzymes: Covalent versus noncovalent catalysis"; Protein Science: A Publication of the Protein Society, 2003. 12(9): p. 2087-2098.

\* cited by examiner

α-tocopherol

α-tocopherol

δ-tocopherol

δ-tocopherol

Mixed tocopherols (Decanox MTS 90G™)

Mixed tocopherols (Decanox MTS 90G™)

MODIFIED LECITHIN, PREPARATION THEREOF, AND USE AS AN ANTIOXIDANT

CROSS REFERENCE TO RELATED APPLICATION

This application claims the benefit of U.S. Provisional Application Ser. No. 62/520,121 filed Jun. 15, 2017 and U.S. Provisional Application Ser. No. 62/612,796 filed Jan. 2, 2018, each of which is hereby incorporated by reference in its entirety.

BACKGROUND

Oils are susceptible to lipid oxidation that causes off flavor, loss of quality and nutrients, and the formation of potentially toxic compounds such as acrolein, 4-hydroxy-2-nonenal (HNE), 4-hydroxy-2-hexenal (HHE), oxidized sterols, and other toxic lipid oxidation products (LOPs). Lipid oxidation is a major challenge faced by the food industry since it causes loss of quality in lipid-containing foods which results in a decrease of shelf life and thus causes food waste. Methods used to inhibit lipid oxidation include metal chelators, control of oxygen concentration, and scavenging of free radicals. Free radical scavengers are one of the major methods of inhibiting lipid oxidation in bulk oils.

In order to delay the oxidation of lipids, food companies make use of free radical scavengers such as BHA (t-butyl-4-hydroxyanisole), BHT (t-butyl-4-hydroxytoluene), and TBHQ (tert-butyl-hydroxyquinone). However, these antioxidants are chemically synthesized and consumers desire simpler and cleaner labels without artificially synthesized antioxidants. Tocopherols are naturally occurring free radical scavengers found in vegetable oils, fish oils and animal fats. Natural antioxidants such as tocopherols provide inherent antioxidant protection to foods and can be added to the food to provide additional protection against lipid oxidation. Unfortunately, natural antioxidants are often not as effective as synthetic antioxidants due to issues such as thermal instability and lower radical scavenging efficiencies, meaning that they must be used at significantly higher concentrations to achieve the same effectiveness as synthetic antioxidants. When tocopherols interact with free radicals, they are consumed and eventually their ability to inhibit lipid oxidation is lost. Adding more tocopherols into oils to prolong antioxidant protection is not effective because tocopherols are pro-oxidative at high concentrations.

The activity of tocopherols can be increased in the presence of compounds that can regenerate oxidized tocopherols back to their original state. Biologically this is done by ascorbic acid (Vitamin C) but this is not possible in food oil applications because ascorbic acid is not lipid soluble. Phosphatidylethanolamine (PE) can also regenerate tocopherols and increase shelf-life, but PE is very expensive, particularly for use as a food additive.

There remains a need in the art for an inexpensive, non-artificial antioxidant product that can significantly improve the shelf life of oils and other lipid-containing materials.

BRIEF SUMMARY

One embodiment is a method of making a modified lecithin comprising conducting an enzymatic conversion of a naturally derived lecithin to form a modified lecithin comprising an enhanced level of phosphatidylethanolamine, phosphatidylserine, or a combination thereof.

Another embodiment is a modified lecithin prepared by a method of conducting an enzymatic conversion of a naturally derived lecithin to form a modified lecithin comprising an enhanced level of phosphatidylethanolamine, phosphatidylserine, or a combination thereof.

In an embodiment, a product or a composition comprises a modified lecithin prepared by a method of conducting an enzymatic conversion of a naturally derived lecithin to form a modified lecithin comprising an enhanced level of phosphatidylethanolamine, phosphatidylserine, or a combination thereof.

In another embodiment, a method of inhibiting or delaying lipid oxidation in a lipid-containing composition comprises incorporating an effective amount of a modified lecithin into a lipid-containing composition, and optionally further incorporating an effective amount of an additional lipid soluble antioxidant into the lipid-containing composition, wherein the modified lecithin is prepared by a method of conducting an enzymatic conversion of a naturally derived lecithin to form a modified lecithin comprising an enhanced level of phosphatidylethanolamine, phosphatidylserine, or a combination thereof.

In yet another embodiment, a modified lecithin comprises an enhanced level of phosphatidylethanolamine and substantially the same amount of phosphatidylinositol, lyso-phospholipids, triglycerols, glycolipids, sterols, carbohydrates, tocopherols, or a combination thereof as compared to the amount of the same components found in a naturally derived, unmodified lecithin.

In yet another embodiment, a modified lecithin comprises an enhanced level of phosphatidylserine and substantially the same amount of phosphatidylinositol, lyso-phospholipids, triglycerols, glycolipids, sterols, carbohydrates, tocopherols, or a combination thereof as compared to the amount of the same components found in a naturally derived, unmodified lecithin.

These and other embodiments are described in detail below.

BRIEF DESCRIPTION OF THE DRAWINGS

The following Figures are exemplary embodiments.

DETAILED DESCRIPTION OF THE INVENTION

Figure 1:
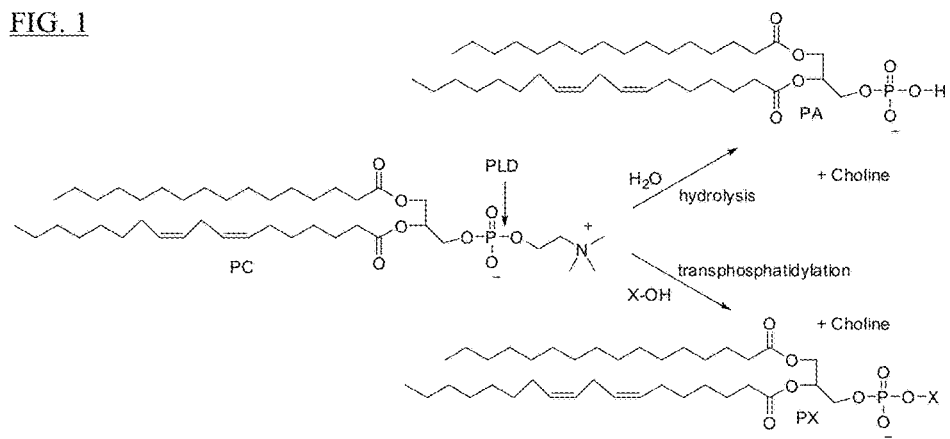
FIG. 1 shows a transphosphatidylation reaction of phosphatidylcholine (PC) to phosphatidyl-X (PX) using a primary alcohol (X—OH) in the presence of phospholipase D (PLD); the figure further shows the hydrolysis reaction of PC to phosphatidyl acid (PA).

Disclosed herein are methods of making a modified lecithin comprising of an enhanced level of phosphatidylethanolamine (PE), phosphatidylserine (PS), or a combination thereof; a modified lecithin; and use of such modified lecithin as an antioxidant to reduce lipid oxidation in a lipid containing material. As used herein, "phosphatidylserine" can mean phosphatidyl-L-serine, phosphatidyl-D-serine, phosphatidyl-DL-serine, or any combination thereof, unless otherwise indicated herein.

Lecithin refers to a mixture of phospholipids extracted from natural sources such as animal (e.g. eggs) and vegetable (e.g. soybean, sunflower, rapeseed and cottonseed) sources. Lecithin from natural sources contain phosphatidylcholine, phosphatidylethanolamine, phosphatidylinositol, phosphatidic acid, lyso-phospholipids, and other components such as triglycerols, glycolipids, sterols, carbohydrates and tocopherols. In an embodiment, the method of making a modified lecithin described herein will change the level of phosphatidylcholine, phosphatidylethanolamine, and phosphatidic acid content of the starting lecithin, but leave the level of remaining components substantially unchanged. In an embodiment, a modified lecithin comprises an enhanced level of phosphatidylethanolamine and substantially the same amount of phosphatidylinositol, lyso-phospholipids, triglycerols, glycolipids, sterols, carbohydrates, tocopherols, or a combination thereof as compared to the amount of the same components found in a naturally derived lecithin. As used herein, "substantially the same amount" means the amount of the individual component in the modified lecithin (e.g. phosphatidylinositol) is within about 10% of the amount found in a naturally derived lecithin.

In an embodiment, the method of making a modified lecithin described herein will change the level of phosphatidylcholine, phosphatidylethanolamine, and phosphatidic acid content of the starting lecithin, but leave the level of remaining components substantially unchanged. In an embodiment, a modified lecithin comprises an enhanced level of phosphatidylserine and substantially the same amount of phosphatidylinositol, lyso-phospholipids, triglycerols, glycolipids, sterols, carbohydrates, tocopherols, or a combination thereof as compared to the amount of the same components found in a naturally derived lecithin.

In general, the modified lecithin is prepared by conducting an enzymatic conversion of a naturally derived lecithin to form a modified lecithin comprising an enhanced level of phosphatidylethanolamine, phosphatidylserine, or a combination thereof. Alternatively, a non-enzymatic hydrolysis process can be used. As used herein, "an enhanced level of phosphatidylethanolamine" means an amount of phosphatidylethanolamine greater than what is present in a naturally derived lecithin. As used herein, "an enhanced level of phosphatidylserine" means an amount of phosphatidylserine greater than what is present in a naturally derived lecithin. Unmodified commercial lecithin contains about 5-40% phosphatidylethanolamine and generally contains less than 15% phosphatidylserine. Lecithins from different sources have varying levels of phospholipids, as shown in the table below, which reports percent of the respective phospholipid based on the total weight of the phospholipids.

|  | Soybean Lecithin | Rapeseed Lecithin | Sunflower Lecithin | Egg Lecithin |
| --- | --- | --- | --- | --- |
| Phosphatidylcholine | 24.1 ± 1.4 | 21.9 ± 1.3 | 31.0 ± 1.8 | 83 |
| Phosphatidylethanolamine | 25.9 ± 1.7 | 12.2 ± 0.8 | 13.8 ± 0.9 | 9 |
| Phosphatidylinositol | 18.2 ± 1.1 | 14.1 ± 0.9 | 23.7 ± 1.4 | 1.2 |
| Phosphatidic acid | 6.1 ± 0.4 | 4.8 ± 0.3 | 5.6 ± 0.4 | 4.2 |
| Other/lyso-phospholipids | 10.9 ± 0.5 | 10.6 ± 0.5 | 3.5 ± 0.2 | 2.6 |

In an embodiment, the modified lecithin comprises greater than 45 weight percent (wt %), greater than 50 wt %, greater than 60 wt %, greater than 70 wt %, or greater than 80 wt % phosphatidylethanolamine based on the total weight of phospholipids present in the modified lecithin.

The enhanced level of phosphatidylethanolamine in the modified lecithin is not created by physical separation of the components found in lecithin or by the addition of phosphatidylethanolamine to the lecithin.

In an embodiment, the modified lecithin comprises greater than 45 weight percent (wt %), greater than 50 wt %, greater than 60 wt %, greater than 70 wt %, or greater than 80 wt % phosphatidylserine based on the total weight of phospholipids present in the modified lecithin.

The enhanced level of phosphatidylserine in the modified lecithin is not created by physical separation of the components found in lecithin or by the addition of phosphatidylserine to the lecithin.

The naturally derived, unmodified lecithin that can be used as the substrate in the enzymatic processes or in the non-enzymatic processes can be made sources such as from soybean, rapeseed, sunflower, corn, fish, krill, egg, etc. or a combination thereof. In an embodiment, the lecithin used as the substrate is a food/cosmetic grade lecithin. The naturally derived lecithin used as the substrate is not purified or isolated phosphatidylcholine.

In an embodiment, the enzymatic conversion involves conducting transphosphatidylation of the phosphatidylcholine present in the naturally derived lecithin using an appropriate phospholipase and ethanolamine to form phosphatidylethanolamine, or serine (L-, D-, or DL-serine) to form a phosphatidylserine. Within this embodiment, the phospholipase is phospholipase D. The phospholipase D can be from microbial or vegetable sources. In the presence of primary alcohols, phospholipase D enzyme catalyzes a transphosphatidylation reaction. The choline head group from phosphatidylcholine is replaced by the alcohol (FIG. 1). When ethanolamine is used as the alcohol, the resulting product is phosphatidylethanolamine and when serine is the alcohol the resulting product is phosphatidylserine.

In an embodiment, the transphosphatidylation reaction is carried out in a bi-phase system. Suitable solvents for the water immiscible phase used to dissolve the lecithin/phospholipid components include an alkyl acetate such as ethyl acetate, n-propyl acetate, n-butyl acetate, isobutyl acetate, and the like; an alkane such as heptane, hexane, pentane, cyclohexane, and the like; a halogenated alkane such as dimethylene chloride, carbon tetrachloride, chloroform, 1,2-dichloroethane, and the like; toluene, xylene, and the like; a water immiscible alkyl ether such as diethyl ether, diisopropylether, and the like. When the modified lecithin will be used in food or cosmetic applications, the solvent for the water immiscible phase is food/cosmetic grade. Within this embodiment, the amount of water can be controlled to minimize the formation of phosphatidic acid. In an embodiment, the amount of water is kept as low as possible.

In another embodiment, the transphosphatidylation reaction is carried out in a mono-phase or single phase system, specifically in the absence of water. Suitable solvents for the single phase system include an alkyl ketone such as acetone and the like; an alkyl acetate such as ethyl acetate, n-propyl acetate, n-butyl acetate, isobutyl acetate, and the like; an alkane such as heptane, hexane, pentane, cyclohexane, and the like; a halogenated alkane such as dimethylene chloride, carbon tetrachloride, chloroform, 1,2-dichloroethane, and the like; toluene, xylene, and the like; an alkyl ether such as diethyl ether, diisopropylether, tetrahydrofuran, and the like. When the modified lecithin will be used in food or cosmetic applications, the solvent for the single phase system is food/cosmetic grade.

The ethanolamine, serine, or other suitable primary alcohol, and phospholipase D can both be found in the aqueous phase. When a modified lecithin having enhanced levels of phosphatidylethanolamine is desired, ethanolamine is used in the transphosphatidylation reaction. Other modified lecithins can be prepared by the transphosphatidylation of the phosphatidylcholine present in the naturally derived lecithin using an appropriate phospholipase and a primary alcohol, such as a C1-C8 alkyl alcohol, where the C1-C8 alkyl alcohol optionally further comprises an amine group. In one embodiment, the primary alcohol is L-serine, D-serine, DL-serine, L-homoserine, D-homoserine, DL-homoserine, and the like.

The temperature of the transphosphatidylation reaction can be carried out at about 4 to about 50° C., specifically about 30 to about 40° C., and more specifically about 35 to about 37° C.

The transphosphatidylation reaction can be monitored for conversion and hydrolysis products and stopped once a desired level of target compound (e.g. phosphatidylethanolamine) is achieved and/or stopped before hydrolysis products such as phosphatidic acid reach undesired levels.

The modified lecithin can be isolated from the reaction mixture by extraction processes, washed with water, and dried using conventional techniques.

In another embodiment, the enzymatic conversion to form a modified lecithin comprising an enhanced level of phosphatidylethanolamine involves conducting demethylation of phosphatidylcholine present in the naturally derived lecithin using an appropriate demethylase to form phosphatidylethanolamine. Exemplary demethylase enzymes that may appropriately demethylate phosphatidylcholine to phosphatidylethanolamine include lanosterol 14α-demethylase.

The modified lecithin comprising an enhanced level of phosphatidylethanolamine, phosphatidylserine, or a combination thereof prepared by the processes described herein can be added to a lipid-containing composition to inhibit or delay lipid oxidation and thereby increase the shelf life of the composition. Any material that has tocopherol containing lipids can benefit from the incorporation of the modified lecithin into the material. Exemplary lipid-containing materials/ingredients can be, or be found in, edible products (food, beverages, and the like), dietary supplements, infant formulas, edible oils, personal care items, cosmetics, medicinal/pharmaceuticals, detergents, soaps, lubricants, paints, plastics, and the like. Exemplary edible products include meat and poultry, fish, seafood, dairy products, low moisture foods including e.g. crackers, snacks, potato chips, etc., frying oils, powders, and the like.

Edible oils include fats and oils obtained from vegetable or animal sources. Exemplary vegetable oils and lipids include canola (rapeseed), coconut, corn, cottonseed, grapeseed, olive, palm, palm kernel, peanut, safflower, soybean, tree nut (almond, Brazil nut, hazelnut, pecan, pine nut, pistachio, walnut), or a combination thereof. Exemplary animal-based oils and lipids include butter, fish oil (bonito, mackerel, salmon, sardine, omega-3 fatty acid oils), lard, poultry fat, milk fat, or a combination thereof. The fats and oils can be in the form of bulk oils or present in mixtures such as oil-in-water emulsions, and the like.

The modified lecithin can be incorporated into the lipid-containing composition in effective amounts suitable for inhibiting or delaying lipid oxidation in the composition. Exemplary amounts of modified lecithin that can be incorporated include about 1 to about 6000 µmol of modified lecithin/kg of lipid-containing composition, specifically about 100 to about 4000 µmol, more specifically about 500 to about 2000 µmol, and still more specifically about 1000 to about 1500 µmol of modified lecithin/kg of lipid-containing composition. In another embodiment, the modified lecithin can be incorporated into the lipid-containing composition along with an additional lipid soluble antioxidant. The additional lipid soluble antioxidant can be added as a separate ingredient, or combined with the modified lecithin to form a modified lecithin composition further comprising the additional lipid soluble antioxidant. Exemplary suitable additional lipid soluble antioxidants include phenolic antioxidants such as tocopherols, specifically α-tocopherol, β-tocopherol γ-tocopherol, δ-tocopherol, or a combination thereof. Tocotrienol homologs may also be suitable antioxidants. In an embodiment, the lipid-containing composition or the product comprising the same may contain an endogenous tocopherol or other antioxidant and therefore may not require the purposeful addition of an additional lipid soluble antioxidant.

Studies suggest that phosphatidylethanolamine has a positive effect on the activity of α-tocopherol whereas phosphatidylcholine has no effect or acts as a pro-oxidant. It has been found that the primary amine present in the headgroup of phosphatidylethanolamine can regenerate oxidized tocopherol quinones through an ionic transfer mechanism. Thus, phosphatidylethanolamine increases the antioxidant activity of tocopherols by regenerating oxidized tocopherol quinones back to the original tocopherol so it can scavenge an additional free radical. Phosphatidylserine can also regenerate tocopherols. Pure phosphatidylethanolamine and phosphatidylserine are too expensive for use as a food additive. Therefore, the modified lecithins described herein provide commercially viable alternatives.

In an embodiment, the lipid-containing composition can comprise an additional lipid soluble antioxidant in an amount of about 1 to about 4000 µmol of the additional lipid soluble antioxidant/kg of lipid-containing composition, specifically about 200 to about 3000 µmol, more specifically about 500 to about 2500 µmol, and still more specifically about 1000 to about 2000 µmol of the additional lipid soluble antioxidant/kg of lipid-containing composition, wherein the amount of additional lipid soluble antioxidant incorporated into the lipid-containing composition does not take into account the presence of endogenous tocopherols that may already be present in the lipid-containing composition.

In an embodiment, a method of inhibiting or delaying lipid oxidation in a lipid containing composition comprises incorporating an effective amount of the modified lecithin described herein into a lipid-containing composition. The modified lecithin can enhance the antioxidant activity of endogenous tocopherol found in the lipid-containing composition to thereby improve the shelf life of the composition. In an alternative embodiment, a method of inhibiting or delaying lipid oxidation in a lipid-containing composition comprises incorporating an effective amount of the modified lecithin described herein into a lipid-containing composition and further incorporating an effective amount of an additional lipid soluble antioxidant (e.g. a tocopherol) into the lipid-containing composition. The modified lecithin and additional lipid soluble antioxidant can be added as separate ingredients or added as a combined mixture.

In another embodiment, phosphatidylcholine present in naturally derived lecithin is enzymatically converted to phosphatidylethanolamine using phospholipase D to form a modified lecithin. The resulting modified lecithin has an increased ability to regenerate tocopherols and similar antioxidants and therefore increase inhibition of lipid oxidation in a lipid containing composition compared to the ability of the naturally derived lecithin to regenerate tocopherols.

Exemplary embodiments are hereby provided.

Embodiment 1

A method of making a modified lecithin, comprising:
conducting an enzymatic conversion of a naturally derived lecithin to form a modified lecithin comprising an enhanced level of phosphatidylethanolamine, a phosphatidylserine (L-, D-, DL-), a phosphatidylhomoserine (L-, D-, DL-), or a combination thereof.

Embodiment 2

The method of EMBODIMENT 1, wherein the modified lecithin comprises greater than 45 wt %, greater than 50 wt %, greater than 60 wt %, greater than 70 wt %, or greater than 80 wt % of the target compound (e.g., phosphatidylethanolamine or phosphatidylserine) based on the total weight of phospholipids present in the modified lecithin.

Embodiment 3

The method of EMBODIMENT 1 or 2, wherein the enzymatic conversion comprises a.) conducting transphosphatidylation of phosphatidylcholine using phospholipase D and a primary alcohol (e.g. ethanolamine, L-serine, D-serine, DL-serine, L-homoserine, D-homoserine, DL-homoserine, a C1-C8 alkyl alcohol, a C1-C8 alkyl alcohol comprising an amine group, and the like); or b.) conducting demethylation of phosphatidylcholine using a demethylase.

Embodiment 4

The method of any one of EMBODIMENTS 1-3, wherein the naturally derived lecithin is from an animal or plant, specifically soybean, rapeseed, sunflower, corn, fish, krill, egg, or a combination thereof.

Embodiment 5

A modified lecithin prepared according to a method of any one of EMBODIMENTS 1-4.

Embodiment 6

A Product Comprising the Modified Lecithin of EMBODIMENT 5, wherein the product can be an edible product, a dietary supplement, an infant formula, an edible oil, a personal care item, a cosmetic, or a medicinal/pharmaceutical.

Embodiment 7

The product of EMBODIMENT 6, wherein the edible oil is a vegetable oil, specifically canola (rapeseed), cocoa butter, coconut, corn, cottonseed, grapeseed, flaxseed (linseed), olive, palm, palm kernel, peanut, safflower, soybean, tree nut (almond, Brazil nut, hazelnut, pecan, pine nut, pistachio, walnut), or a combination thereof; or an animal-based oil, specifically butter, fish oil (bonito, mackerel, salmon, sardine, omega-3 fatty acids), lard, poultry fat, milk fat, or a combination thereof.

Embodiment 8

A modified lecithin composition, comprising the modified lecithin of EMBODIMENT 5 and an additional lipid soluble antioxidant.

Embodiment 9

The modified lecithin composition of EMBODIMENT 8, wherein the additional lipid soluble antioxidant is a tocotrienol homolog, a tocopherol, specifically α-tocopherol, β-tocopherol γ-tocopherol, δ-tocopherol, an endogenous tocopherol, or a combination thereof.

Embodiment 10

A method of inhibiting or delaying lipid oxidation in a lipid-containing composition, comprising:
incorporating an effective amount of the modified lecithin of EMBODIMENT 5 into a lipid-containing composition, and optionally further incorporating an effective amount of an additional lipid soluble antioxidant into the lipid-containing composition or utilizing endogenous tocopherol already in the product.

Embodiment 11

The method of EMBODIMENT 10, wherein the modified lecithin is incorporated in an amount of about 1 to about 6000 µmol of modified lecithin/kg of lipid-containing composition, specifically about 100 to about 4000 µmol, more specifically about 500 to about 2000 µmol, and still more specifically about 1000 to about 1500 µmol of modified lecithin/kg of lipid-containing composition.

Embodiment 12

The method of EMBODIMENT 10 or 11, wherein the lipid-containing composition further comprises an additional lipid soluble antioxidant in an amount of about 1 to about 4000 μmol of the additional lipid soluble antioxidant/kg of lipid-containing composition, specifically about 200 to about 3000 μmol, more specifically about 500 to about 2500 μmol, and still more specifically about 1000 to about 2000 μmol of the additional lipid soluble antioxidant/kg of lipid-containing composition, wherein the amount of additional lipid soluble antioxidant incorporated into the lipid-containing composition does not take into account the presence of endogenous tocopherols that may already be present in the lipid-containing composition.

Embodiment 13

The method of any one of EMBODIMENTS 10-12, wherein the additional lipid soluble antioxidant is a tocotrienol homolog, a tocopherol, specifically α-tocopherol, β-tocopherol γ-tocopherol, δ-tocopherol, an endogenous tocopherol, or a combination thereof.

Embodiment 14

The method of any one of EMBODIMENTS 10-13, wherein the lipid-containing composition is an edible product, a dietary supplement, an infant formula, an edible oil, a personal care item, a cosmetic, or a medicinal/pharmaceutical, or an ingredient thereof.

Embodiment 15

The method of EMBODIMENT 14, wherein the lipid-containing composition is a vegetable oil, specifically canola (rapeseed), cocoa butter, coconut, corn, cottonseed, grapeseed, flaxseed (linseed), olive, palm, palm kernel, peanut, safflower, soybean, tree nut (almond, Brazil nut, hazelnut, pecan, pine nut, pistachio, walnut), or a combination thereof; or an animal-based oil, specifically butter, fish oil (bonito, mackerel, salmon, sardine, omega-3 fatty acids), lard, poultry fat, milk fat, or a combination thereof.

Embodiment 16

The method of EMBODIMENT 14, wherein the lipid-containing composition is an oil-in-water emulsion, or a lipid containing food, such as meats, seafood, low moisture foods, pet foods, medical foods, nut products, and the like, or a combination thereof.

Embodiment 17

A modified lecithin, comprising an enhanced level of phosphatidylethanolamine, phosphatidylserine, or a combination thereof, and substantially the same amount of phosphatidylinositol, lyso-phospholipids, triglycerols, glycolipids, sterols, carbohydrates, tocopherols, or a combination thereof as compared to the amount of the same components found in a naturally derived, unmodified lecithin.

Embodiment 18

The modified lecithin of EMBODIMENT 17, comprising greater than 45 wt %, greater than 50 wt %, greater than 60 wt %, greater than 70 wt %, or greater than 80 wt % phosphatidylethanolamine, phosphatidylserine, or a combination thereof, based on the total weight of phospholipids present in the modified lecithin.

The modified lecithin, methods of making, and use for inhibiting or delaying lipid oxidation in a lipid-containing composition are further illustrated by the following non-limiting examples.

EXAMPLES

Example 1. Enzymatic Modification of Lecithin Using Phospholipase D

A study was conducted to explore the conversion of phosphatidylcholine (PC) present in egg yolk lecithin to phosphatidylethanolamine (PE) using phospholipase D (PLD) to result in the preparation of a modified lecithin.

Materials: Lecithin (egg, 70% PC), enzyme phospholipase D (PLD, >50,000 units per mL), and ethanolamine were purchased from Sigma-Aldrich Co. (St. Louis, Mo., USA). All other reagents were of analytical grade or high-performance liquid chromatography (HPLC) grade; water was distilled water.

Procedure: A PLD solution is prepared by mixing 5 μl of PLD with 200 μl buffer solution (pH 8.0, 0.2 M sodium acetate buffer, with 0.01 M CaCl2). The prepared PLD solution was kept at 4° C. and used within 1 hour after dilution.

Lecithin (0.3 g) was dissolved in 30 ml of ethyl acetate (ultrasonicated if necessary) and a mixture of ethanolamine and hydrochloric acid (1.0 ml of hydrochloric acid was drop wisely added into 3.0 ml of ethanolamine, in ice-bath) was added. As ethanolamine is an organic base (pKa 9.5), ethanolamine was neutralized with hydrochloric acid to minimize its influence on the pH of the system. The mixture was agitated with magnetic stirrer and 0.2 ml PLD solution was then added to start enzymatic reaction. The mixture was kept at 37° C. for the 40 min. Water content would significantly influence the enzymatic modification products. Higher water ratio would increase the content of phosphatidyl acid (PA) in final products. Additionally, control of the time of the reaction would provide lecithin with different PE %, but too much time could also increase PA %.

After the enzymatic reaction, the organic phase was collected and rotary evaporated at 30° C. to remove the organic solvents. The residue was combined with the water phase and kept at −18° C. A solvent (Chloroform-methanol-water (80:30:20, v/v) was added to extract the modified lecithin. The organic phase was collected and the water phase was further extracted with 50 ml of chloroform. The organic extractions were combined and back extracted with 30 ml of water to remove water-soluble components. Then the solution was dehydrated with anhydrous Na2SO4 and rotary evaporated at 30° C. after filtration. The residue was further vacuum dried at 40° C. to remove water and solvents if necessary.

Table 1 reports the results of the conversion in terms of percent of PC, PE, and lyso phosphatidylcholine (lysoPC).

TABLE 1

Phospholipid concentration before and after modification of egg lecithin

| Lecithin | PC % | PE % | lysoPC % |
| --- | --- | --- | --- |
| Egg lecithin (Sigma) | 70 | 14 | 3 |
| Modified lecithin using PLD | 4.2 | 94.2 | 3 |

Example 2. Enzymatic Modification of Lecithin Using Phospholipase D

A study was conducted to explore the conversion of phosphatidylcholine (PC) present in egg yolk lecithin to phosphatidylethanolamine (PE) using phospholipase D (PLD) at varying pH conditions to result in the preparation of modified lecithin.

Materials: Lecithin (~60% L-α-phosphatidylcholine) from egg yolk was purchased from Sigma-Aldrich Co. (St. Louis, Mo., USA). 1,2-Dioleoyl-sn-glycero-3-phosphocholine (DOPC) and 1,2-dioleoyl-sn-glycero-3-phosphoethanolamine (DOPE) were purchased from Avanti Polar Lipids, Inc. (Alabaster, Ala., USA). The enzyme phospholipase D from *Streptomyces chromofuscus* (>50,000 units per mL) was purchased from Sigma-Aldrich Co. (St. Louis, Mo., USA). The solvent ethyl acetate was purchased from Fischer Scientific (Pittsburgh, Pa., USA). All other reagents were of HPLC grade or purer. Distilled and deionized water was used throughout.

Methods: The phospholipase D enzyme solution was prepared immediately before each experiment. Phospholipase D was dissolved in 0.2 mL of 0.2 M sodium acetate (pH 8.0) with 0.01M calcium chloride to obtain ~250 units of activity. The enzyme solution was stored at 4° C. and used within 1 hour. Lecithin (0.3 g) was dissolved in 30 mL of ethyl acetate. An ethanolamine hydrochloric acid mixture was prepared by adding 1.0 mL of hydrochloric acid drop wise to 3.0 mL of ethanolamine placed in an ice bath. The ethanolamine hydrochloric acid mixture was added to the lecithin dissolved in the ethyl acetate. The enzymatic reaction was started by adding the 0.2 mL of phospholipase D solution to this mixture. The reaction was carried out at 37° C. for 40 minutes with continuous stirring.

After the enzymatic reaction, the organic phase was isolated using a separating funnel. The organic phase was evaporated with a rotary evaporator (Brinkman, Flawil, Switzerland) at 40° C. The resulting residue was recombined with the water phase and 80 mL chloroform, 30 mL methanol, and 20 mL of water was added. The organic phase was separated from the water phases using a separating funnel. The water phase was further extracted using 50 mL chloroform and this chloroform was combined with the organic phase. The total organic phase was extracted with 30 ml water to remove the remaining water soluble components. The organic phase was evaporated at 40° C. using the rotary evaporator and then vacuum dried with a Savant™ centrifugal vacuum concentrator (Thermo Fischer, Waltham, Mass., US) to get the lecithin solids.

The phospholipids in the lecithin were quantified using HPLC. Sample was dissolved in acetonitrile (~500 ppm) and 10 μL was injected into a Shimadzu (Kyoto, Japan) HPLC system after passing the sample through a 0.2 μm filter (Merck Millipore Ltd., Darmstadt, Germany). HPLC used a Phenomenex Luna NH2 column (150 mm×4.6 mm, 5 μm). This column comprises of silica surface covered with cross-linked diol groups which helps in separating polar compounds. The flow was set up in gradient mode going from 5% water and 95% acetonitrile and then to 50% water and 50% acetonitrile over 15 minutes. The phospholipids were detected using an evaporative light scattering detector operating at 30° C. Standard 1,2-dioleylphosphatidylcholine, 1,2-dioleylphoshphatidylethanolamine, and 1,2-dioleylphosphatidic acid were used to prepare the standard curves. The phospholipids in the lecithin were identified and quantified by using the relative retention times and peak areas of the standards.

Results: Selection of pH. Ethanolamine is an organic base which changed the pH of the system (0.2 ml Buffer+3.0 ml ethanolamine) to 12.6. This high pH could be outside of the optimum of the enzyme so the impact of additional pH values on PC to PE conversion were tested. Addition of 1 and 3 mL of 12 N HCl decreased the pH to 10.3 and 9.1, respectively. Phospholipase D has been reported to possess a maximum activity at pH 8 with pure PC [Yang, H. and M. F. Roberts, Phosphohydrolase and transphosphatidylation reactions of two *Streptomyces* phospholipase D enzymes: Covalent versus noncovalent catalysis. Protein Science: A Publication of the Protein Society, 2003. 12(9): p. 2087-2098; Imamura, S. and Y. Horiuti, Enzymatic Determination of Phospholipase D Activity with Choline Oxidase. The Journal of Biochemistry, 1978. 83(3): p. 677-680], but in the presence of lecithin, maximal conversion of PC to PE was observed at pH 10.3. Table 2 reports the results of the conversion under various pH. Decreasing pH to 9.1 did result in PE formation but also resulted in large amounts of phosphatidic acid (PA). Not wishing to be bound by theory, but this result could be because higher amount of hydrochloric acid needed to decrease the pH increased the ratio of water in the system and induced hydrolysis of phospholipids.

TABLE 2

Phospholipid concentration before and after modification of egg lecithin using different amounts of hydrochloric acid

| pH | Volume of HCl (mL) | PE % | PC % | PA % |
|---|---|---|---|---|
| Before modification | | 33.4 | 61.7 | 0.1 |
| 12.6 | 0 | 62 | 3.2 | 34.1 |
| 10.3 | 1 | 89.9 | 3.0 | 7.1 |
| 9.1 | 3 | 47.4 | 15.1 | 34.3 |

Example 3. Impact of Modified Lecithin on Stripped Soybean Oil Oxidation

Figure 2:
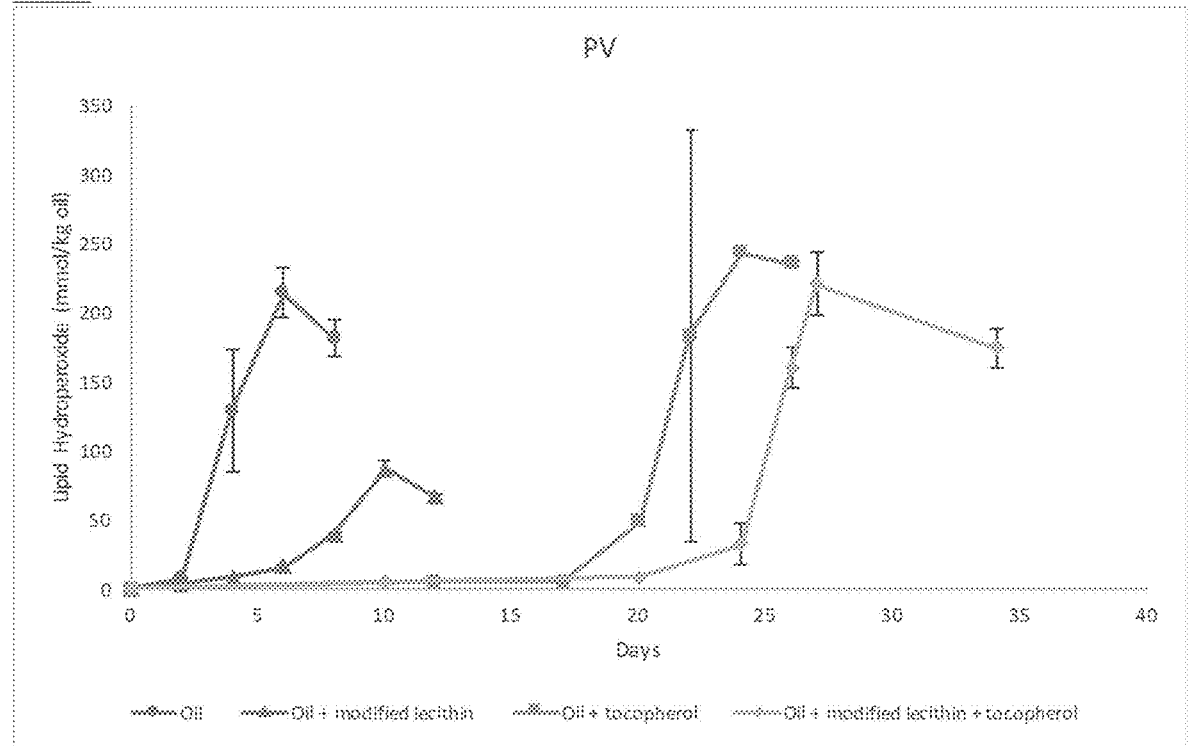
FIG. 2 shows the formation of lipid hydroperoxides (peroxide value (PV)) of stripped soybean oil with Control (Oil); Oil+modified lecithin; Oil+α-tocopherol; and Oil+α-tocopherol+modified lecithin at 55° C.; data points represent means (n=3)±standard deviations.
Figure 3:
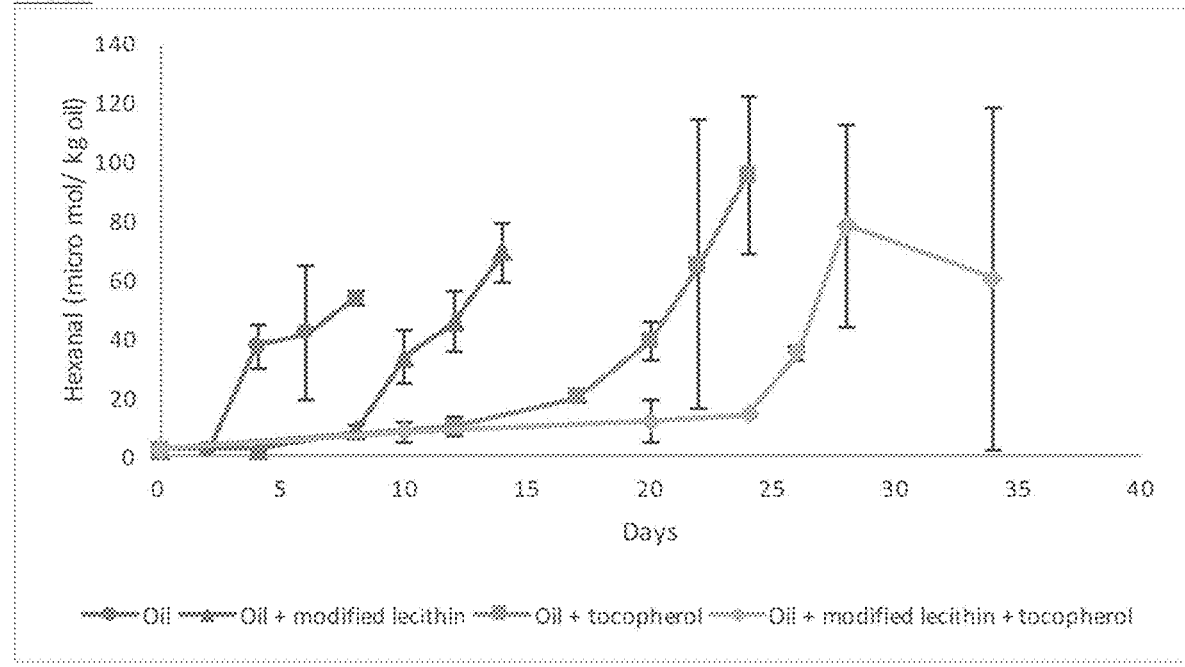
FIG. 3 shows the headspace hexanal of stripped soybean oil with Control (Oil); Oil+modified lecithin; Oil+α-tocopherol; and Oil+α-tocopherol+modified lecithin at 55° C.; data points represent means (n=3)±standard deviations.
Figure 4A:
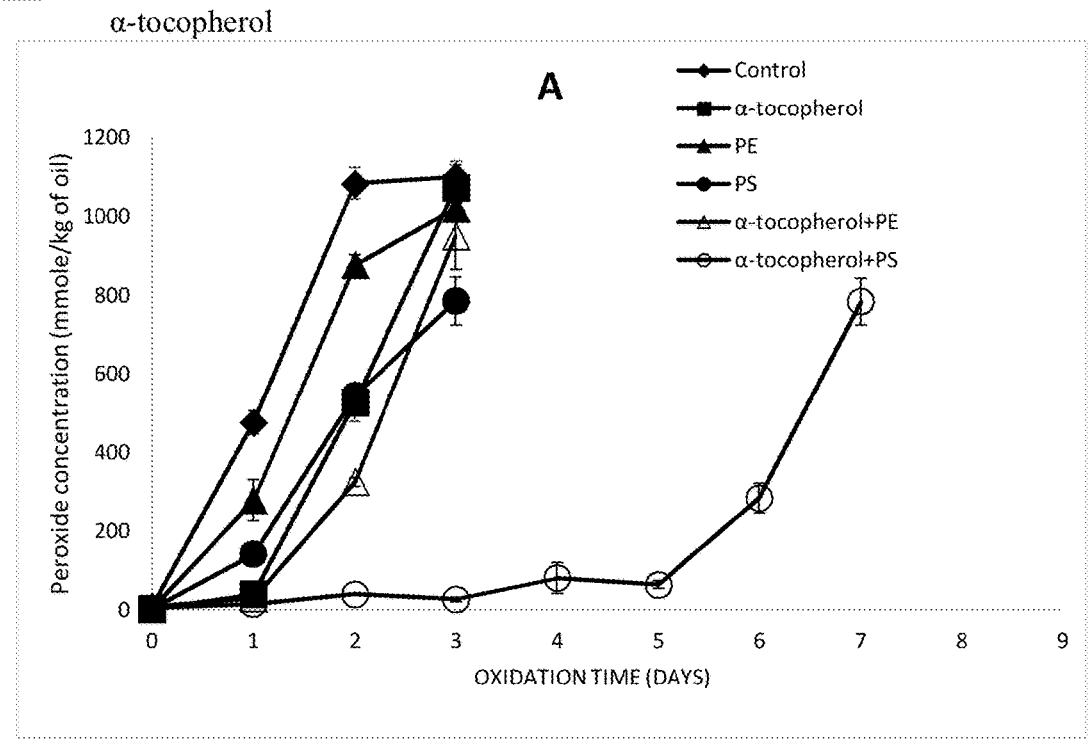
FIGS. 4A and 4B show the formation of lipid hydroperoxides (4A) and hexanal (4B) in 1% stripped soybean O/W emulsion containing 3.0 µmol/kg emulsion α-tocopherol and 15.0 µmol/kg emulsion PE or PS with TWEEN 20 as emulsifier. Each value represents the mean (n=3)±standard deviations.
Figure 4B:
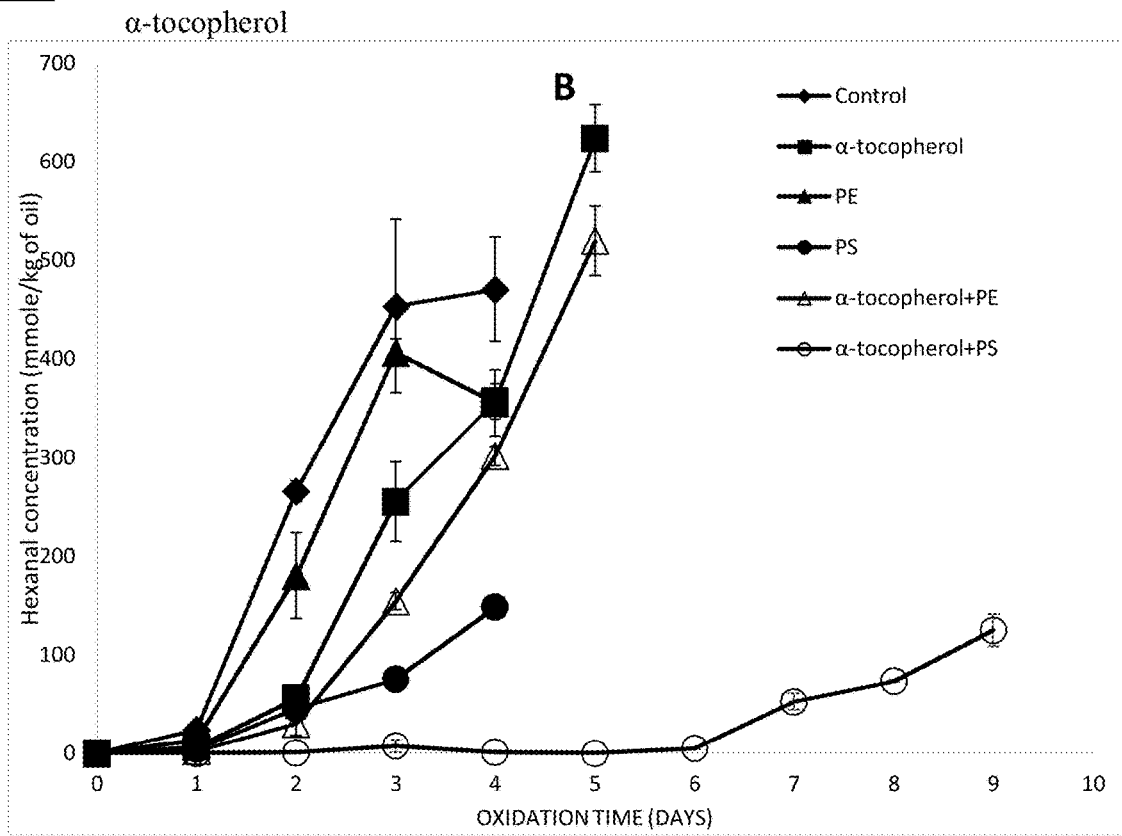
Figure 5A:
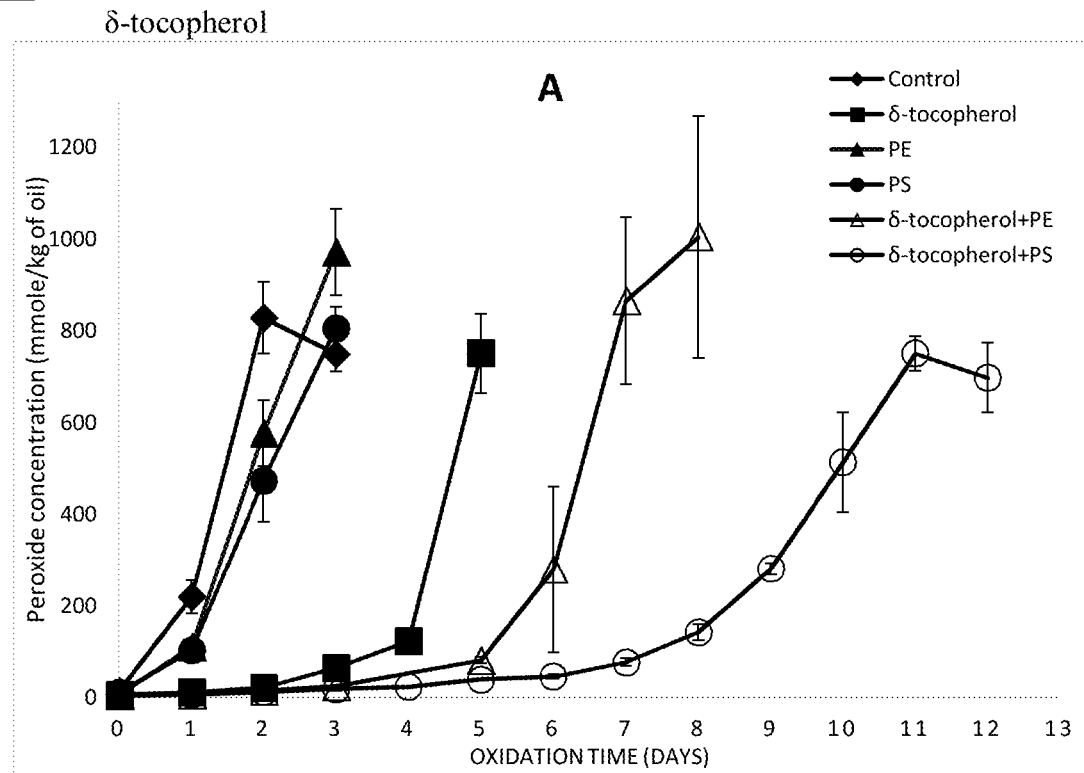
FIGS. 5A and 5B show formation of lipid hydroperoxides (5A) and hexanal (5B) in 1% stripped soybean O/W emulsion containing 3.0 µmol/kg emulsion δ-tocopherol and 15.0 µmol/kg emulsion PE or PS with TWEEN 20 as emulsifier. Each value represents the mean (n=3)±standard deviations.
Figure 5B:
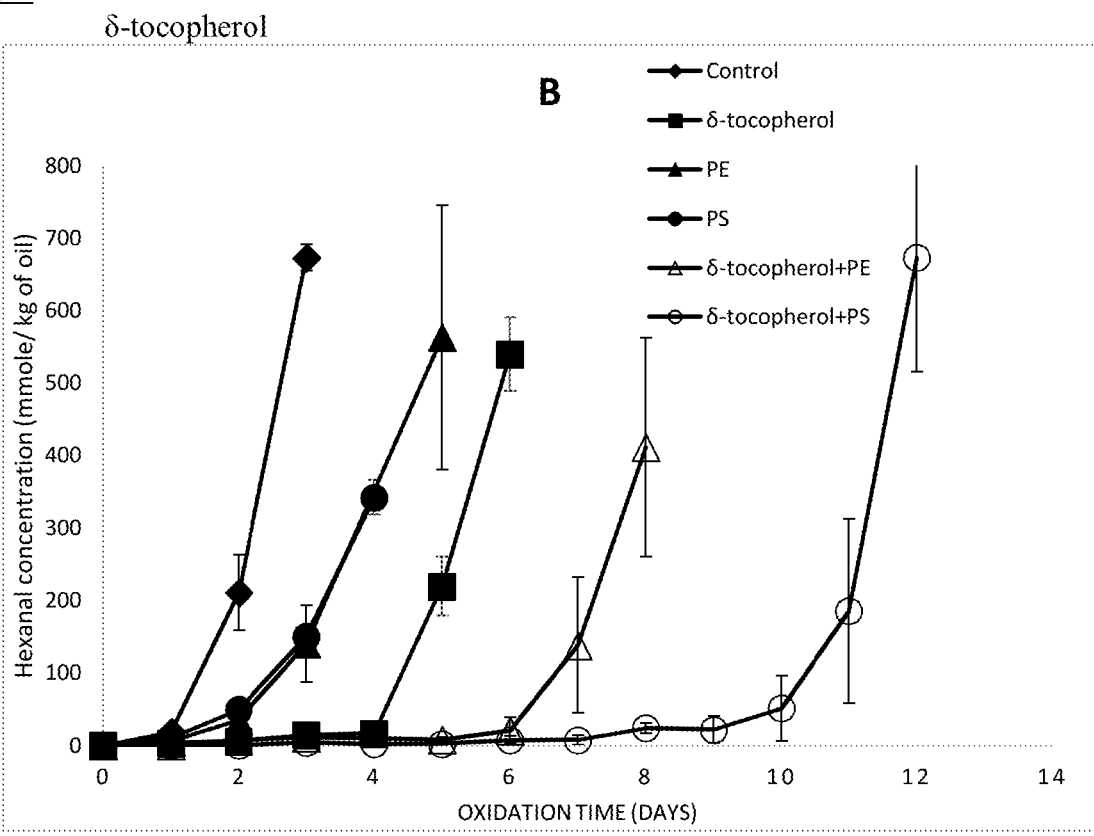
Figure 6A:
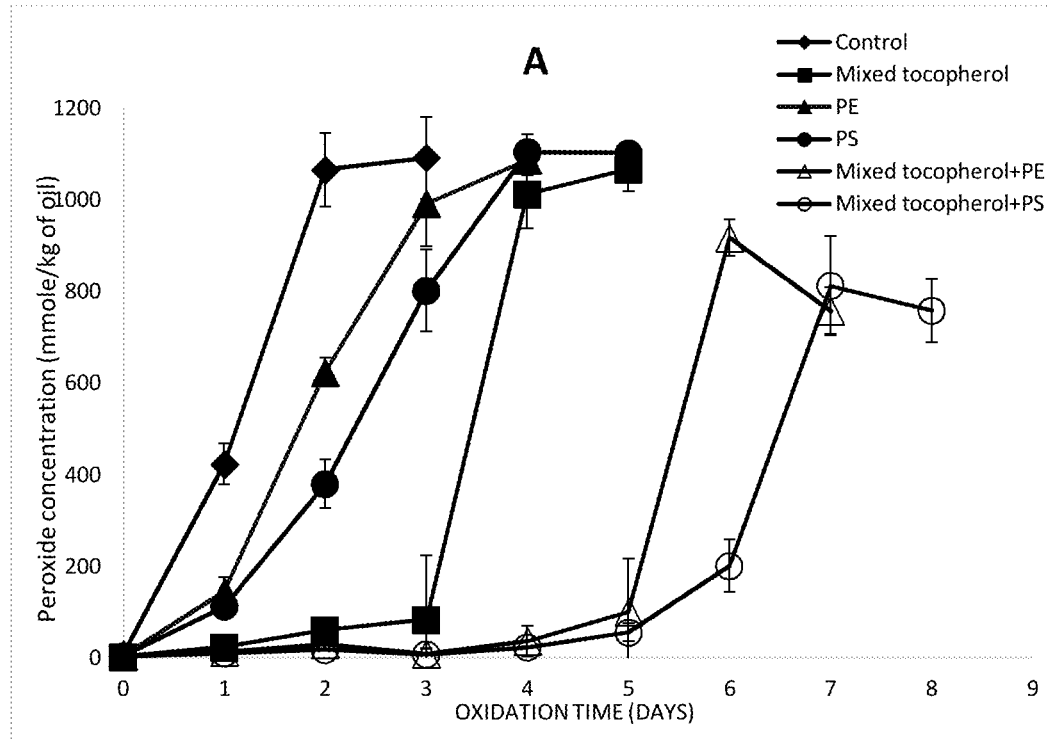
FIGS. 6A and 6B show formation of lipid hydroperoxides (6A) and hexanal (6B) in 1% stripped soybean O/W emulsion containing 3.0 µmol/kg emulsion mixed tocopherol and 15.0 µmol/kg emulsion PE or PS with TWEEN 20 as emulsifier. Each value represents the mean (n=3)±standard deviations.
Figure 6B:
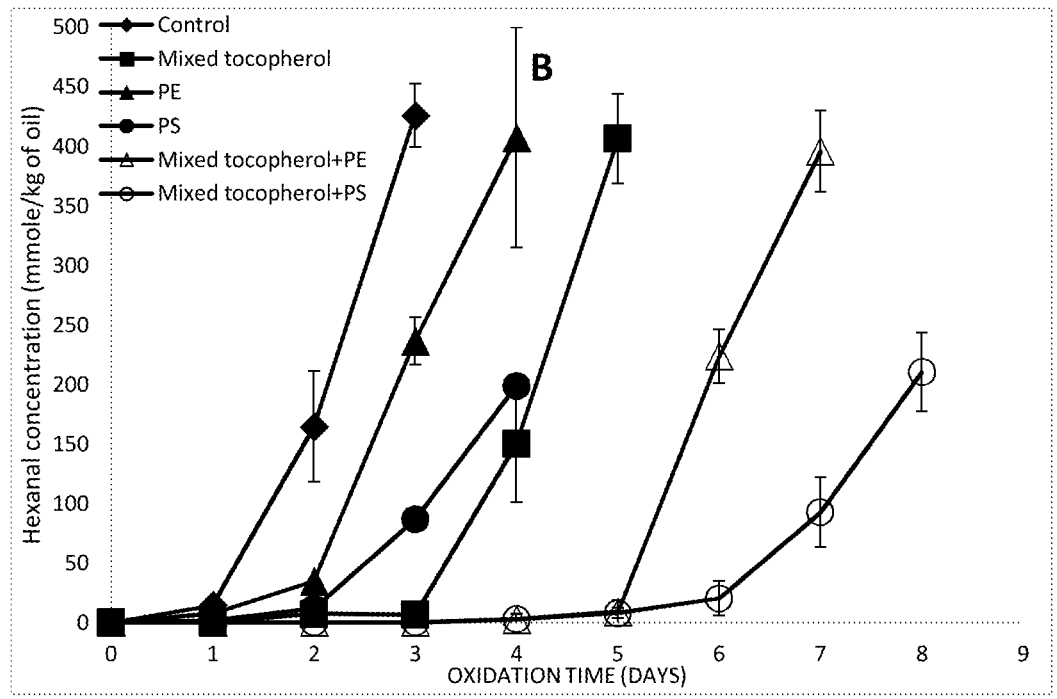
Figure 7A:
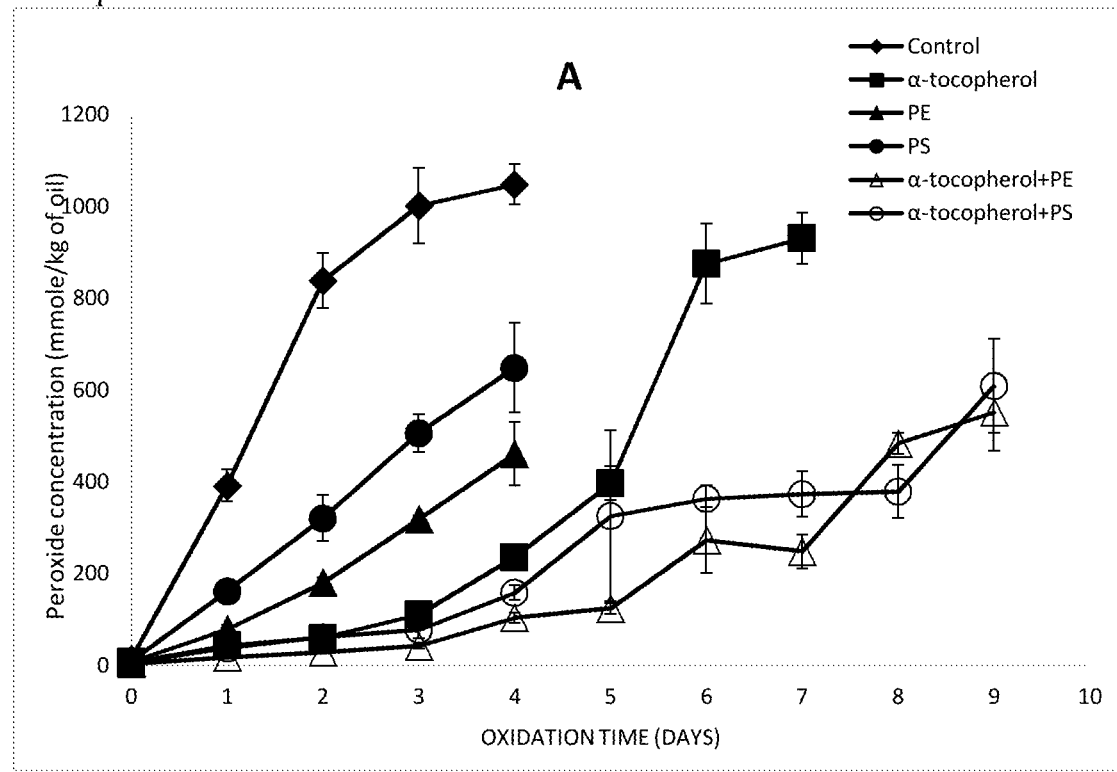
FIGS. 7A and 7B show formation of lipid hydroperoxides (7A) and hexanal (7B) in 1% stripped soybean O/W emulsion containing 3.0 µmol/kg emulsion α-tocopherol and 15.0 µmol/kg emulsion PE or PS with BSA as emulsifier. Each value represents the mean (n=3)±standard deviations.
Figure 7B:
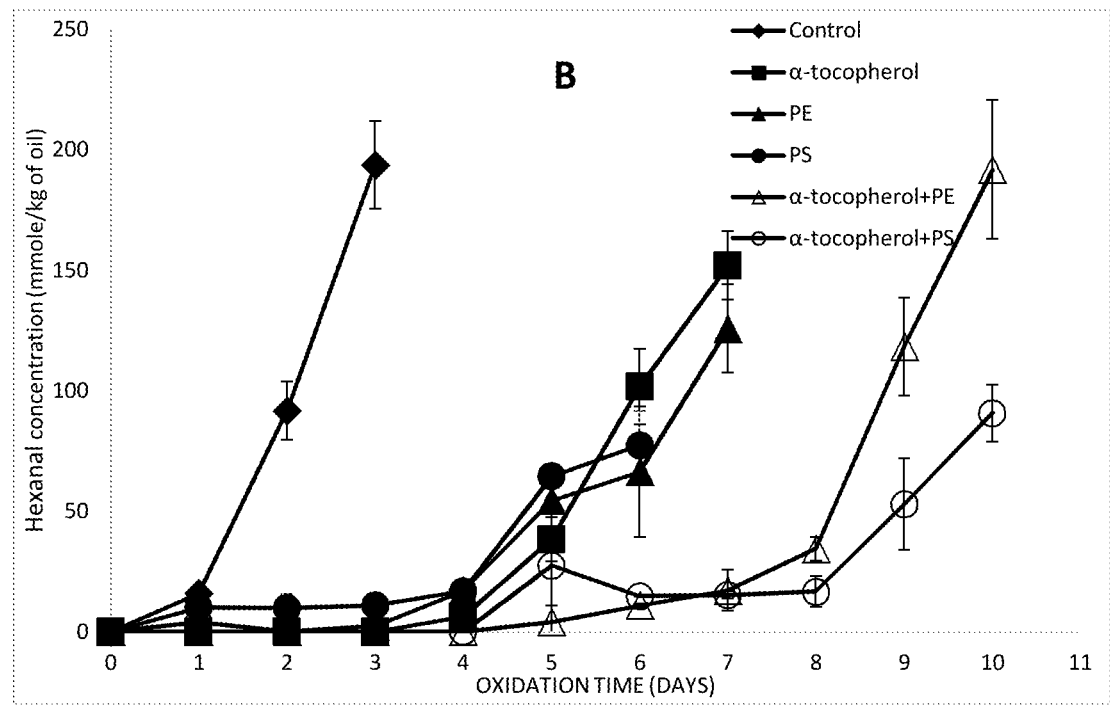
Figure 8A:
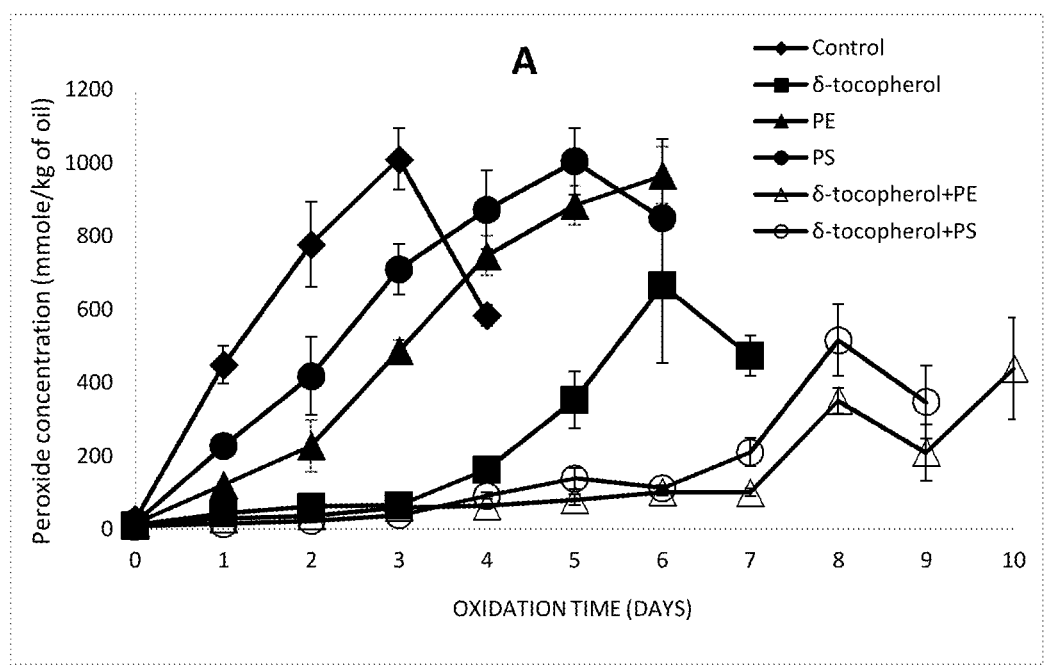
FIGS. 8A and 8B show formation of lipid hydroperoxides (8A) and hexanal (8B) in 1% stripped soybean O/W emulsion containing 3.0 µmol/kg emulsion δ-tocopherol and 15.0 µmol/kg emulsion PE or PS with BSA as emulsifier. Each value represents the mean (n=3)±standard deviations.
Figure 8B:
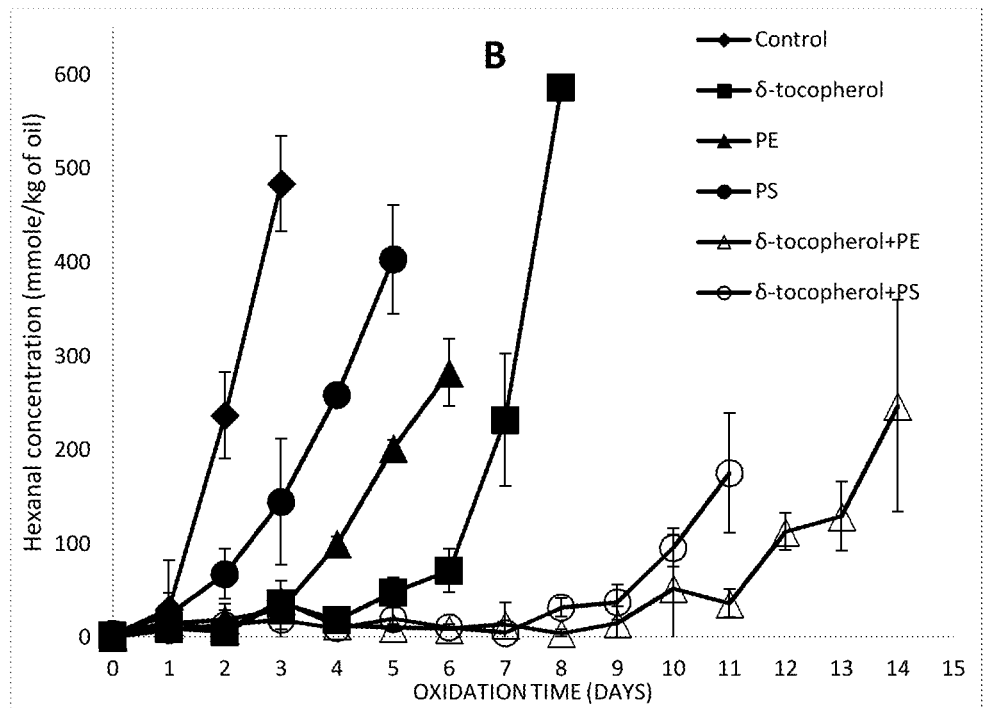
Figure 9A:
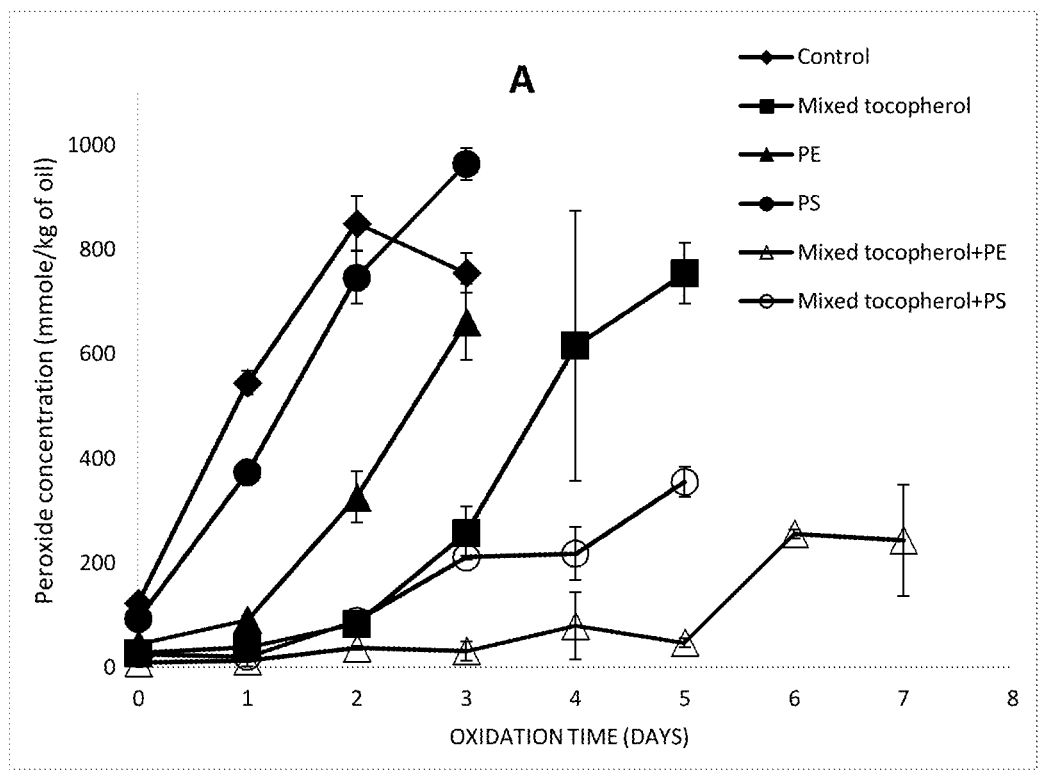
FIGS. 9A and 9B show formation of lipid hydroperoxides (9A) and hexanal (9B) in 1% stripped soybean O/W emulsion containing 3.0 µmol/kg emulsion mixed tocopherol and 15.0 µmol/kg emulsion PE or PS with BSA as emulsifier. Each value represents the mean (n=3)±standard deviations.
Figure 9B:
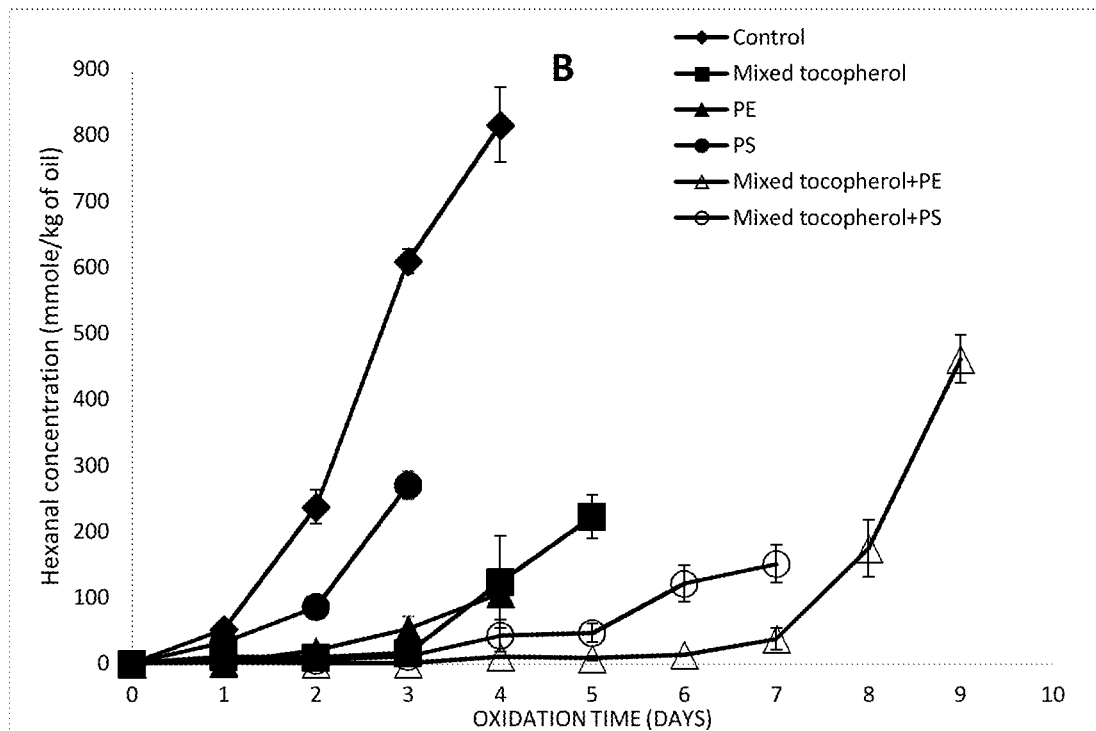

The effect of modified lecithin prepared in accordance with Example 1, used alone and combined with tocopherol, on the inhibition of lipid oxidation of a lipid system was studied. Four samples were studied, i) stripped soybean oil (SSO) and medium chain triglycerides (MCT) (25:75) ("Oil", Control); ii) the Oil and 1000 μmol modified lecithin/kg of oil; iii) the Oil along with 100 μmol α-tocopherol/kg oil; and iv) the Oil along with 100 μmol α-tocopherol/kg oil and 1000 μmol modified lecithin/kg of oil. FIG. 2 reports the formation of lipid hydroperoxides and FIG. 3 reports headspace hexanal of SSO with Control (Oil); Oil+modified lecithin; Oil+α-tocopherol; and Oil+α-tocopherol+modified lecithin at 55° C. Data points represent means (n=3)±standard deviations.

As expected, α-tocopherol inhibited lipid oxidation as can be seen by the lag phases of both lipid hydroperoxide (FIG. 2) and hexanal formation (FIG. 3) increasing to 18 and 20 days, respectively compared to 3 days (both lipid hydroperoxide and hexanal) for the Control. The results also showed that the lecithin worked together with α-tocopherol increasing the lag phases of the hydroperoxide and hexanal formation to 26 and 25 days respectively.

Example 4. Impact of PE and PS to Enhance the Antioxidant Activity of Tocopherols in Oil-in-Water Emulsions While PE and PS have been shown to increase the antioxidant activity of tocopherols in bulk oil, no research has been conducted on the ability of PE and PS to enhance the antioxidant activity of tocopherols in oil-in-water emulsions. This work is important because while tocopherols and PS could easily interact in bulk oils, this might not be true in oil-in-water emulsions where the phospholipids and tocopherols could partition in different phases (e.g. emulsion droplet core, interface, or aqueous phase) thus inhibiting the ability of the phospholipids to interact with tocopherols and tocopherol quinones. Therefore, the objective of this study is to determine if PE and PS can enhance the antioxidant activity of tocopherols in oil-in-water emulsions and understand the effect of different tocopherol homologue and emulsifier type on the ability of PE and PS to act synergistically with tocopherols in delaying lipid oxidation.

Materials and Methods:

Soybean oil was purchased from a local store and stored at −20° C. until use. 1,2-Dioleoyl-sn-glycero-3-phosphoethanolamine (PE) and 1,2-dioleoyl-sn-glycero-3-phosphor-L-serine sodium salt (PS) were purchased from Avanti Polar Lipids, Inc. (Alabaster, Ala., USA). TWEEN 20 (polyethylene glycol sorbitan monolaurate), bovine serum albumin (BSA), silicic acid, activated charcoal, α-tocopherol, α-tocopherol quinone and 6-tocopherol were purchased from Sigma-Aldrich Co. (St. Louis, Mo., USA). Mixed tocopherols, Decanox MTS-90G, were donated by Archer Daniels Midland (Chicago, Ill., USA). This mixture of tocopherols was 92.7% pure and consisted of 697 mg γ-tocopherol, 134 mg of δ tocopherol, 151 mg of β-tocopherol+δ tocopherol and 79 mg α-tocopherol per gram as provided by the manufacturer. Molecular weight of mixed tocopherols were calculated by multiplying the relative fraction of each tocopherol homologue in the mixture with its own molecular weight and adding all homolog concentrations together. All other reagents were of HPLC grade or purer. Distilled and deionized water was used in all experiments. Glassware was soaked overnight in 2N hydrochloric acid to remove metals, rinsed with distilled and deionized water and dried before use.

Preparation of Stripped Soybean Oil (SSO):

In order to study tocopherol and phospholipid interactions without the interference of other oil components, a chromatographic column was used to separate soybean oil triacylglycerols from minor oil components like tocopherols, phospholipids, free fatty acids and mono and diacylglycerols according to the method reported by Cui et al. "Impact of phosphatidylethanolamine on the antioxidant activity of α-tocopherol and trolox in bulk oil." *Journal of agricultural and food chemistry.* 2015; 63(12):3288. This method confirmed the effectiveness of stripping by showing undetectable tocopherol levels after the procedure was completed. Briefly, three layers were packed into a chromatographic column (3.0 cm internal diameter×35 cm height). The bottom layer was packed with 22.5 g of silicic acid (washed with distilled and deionized water and activated at 110° C. for 24 h). Activated charcoal (5.6 g) was then used for the middle layer and another 22.5 g of silicic acid for the top layer. Commercial soybean oil (30 g) was mixed with 30 mL of hexane and the triacylglycerol fraction was eluted from the column using 270 ml of hexane. The solvent was then removed by a vacuum rotary evaporator (Rotavapor R 110, Buchi, Flawil, Switzerland) at 25° C., and the remaining solvent was evaporated by nitrogen flushing. Stripped soybean oil was stored at −80° C. in the dark until emulsions were prepared.

Emulsion Preparation and Storage Conditions:

Oil-in-water (O/W) emulsions were prepared using 1.0 wt % stripped soybean oil and 10 mM imidazole-acetate buffer, pH 7. TWEEN 20 or BSA was used as the emulsifier at a 1:10 emulsifier:oil ratio. The emulsion was prepared by adding phospholipids (15.0 µmole/kg of emulsion) dissolved in chloroform with or without tocopherols (3.0 µmole/kg of emulsion) dissolved in methanol into a beaker and flushing with nitrogen gas to remove the solvents. Stripped soybean oil was then added to the beaker and stirred at room temperature for 30 min. TWEEN 20 and imidazole acetate buffer were mixed in a separate beaker and then added to the beaker containing stripped soybean oil and a coarse emulsion was made by blending with a hand-held homogenizer (M133/1281-0, Biospec Products Inc., Bartlesville, Okla.) for 2 mins. The coarse emulsion was then homogenized with a microfluidizer (Microfluidics, Newton, Mass., USA) at a pressure of 9 kpsi for three passes. During homogenization, ice was used to cover the homogenizer chamber and coil, to keep the emulsion cold. One milliliter of each emulsion was transferred into 10 mL GC vials (Supelco), capped with aluminum lids having PTFE/silicone septa and stored in the dark at 20° C.

Evaluation of Particle Size Distributions and Zeta Potential:

Samples for droplet size distribution and zeta potential measurements were prepared by diluting the emulsion 10 times into 10 mM imidazole acetate buffer pH 7.0. Both particle size distributions and zeta potential of the emulsions were analyzed in a ZetaSizer Nano-ZS (Malvern Instruments, Worcestershire, UK) (Johnson et al. "Development of iron-chelating poly(ethylene terephthalate) packaging for inhibiting lipid oxidation in oil-in-water emulsions." *Journal of agricultural and food chemistry.* 2015; 63(20):5055. The particle size and zeta potential were determined right after emulsion preparation and at the end of each experiment. Each measurement was repeated thrice at room temperature.

Evaluation of Lipid Oxidation:

Formation of primary and secondary (lipid hydroperoxides and hexanal, respectively) lipid oxidation products were quantified to determine the oxidative stability of the O/W emulsions. Lipid hydroperoxides were quantified using a modified version of the method reported by Shantha and Decker "Rapid, sensitive, iron-based spectrophotometric methods for determination of peroxide values of food lipids." *JAOAC Int.* 1994; 77(2):421-424. Emulsions (0.3 mL) were vortexed three times (10 s each) with 1.5 mL of an iso-octane:iso-propanol (3:1, v/v) solution. The samples were then centrifuged for 2 min at 3,000 rpm (Centrific™ Centrifuge, Fisher Scientific, Fairlawn, N.J.) after which 0.2 mL of the upper organic layer was mixed with 2.8 mL of methanol:butanol solution (2:1, v/v), 15 uL of 3.94 M ammonium thiocyanate and 15 uL of a ferrous iron solution. The ferrous iron solution was prepared by mixing 0.132 M $BaCl_2$ and 0.144 M $FeSO_4$. Twenty min. after iron addition, the absorbance of the samples was measured at 510 nm, using a Genesys 20 spectrophotometer (Thermo-Spectronic, Waltham, Mass.). Hydroperoxide levels were quantified from a cumene hydroperoxide standard calibration curve.

Headspace hexanal was quantified using a method described by Cardenia et al. "Antioxidant and prooxidant activity behavior of phospholipids in stripped soybean oil-in-water emulsions." *J Am Oil Chem Soc.* 2011; 88(9):1409-1416 using solid-phase microextraction-head space gas chromatography with flame ionization detection (SPME-GC-FID). The gas chromatograph was a Shimadzu GC-2014 (Shimadzu, Kyoto, Japan) equipped with an AOC-5000 autosampler (Shimadzu) and a split-splitless injector. An Equity DB-1 column (30 m×0.32 mm×1 mm film thickness, Supelco, Bellefonte, Pa.), was used for separation of volatiles. Samples were shaken and heated at 55° C. for 10 min. in an autosampler heating block before injection. A 50/30 mm divinylbenzene/carboxen/polydimethylsiloxane SPME fiber needle (Supelco, Bellefonte, Pa.) was introduced into the vial for 2 min. to absorb volatiles and then was transferred to the injector port to allow volatile desorption for 3 min. at 250° C. Oven temperature was 65° C. and run time was 6 min. The injector and detector temperatures were both set at 250° C. Helium was used as carrier gas at a flow rate of 1.0 mL/min. with a split ratio of 1:7. Hexanal concentrations were determined from peak areas using a calibration curve prepared with hexanal standard solutions. Both lipid hydroperoxides and headspace hexanal were determined on the day of emulsion preparation (day 0) and then every 24 hours.

Interaction Index:

To find out if interactions between antioxidants was synergistic, the interaction index was calculated as: {(observed lag phase of combination−lag phase of control)/[(lag phase of tocopherol alone−lag phase of control)+(lag phase of phospholipid alone−lag phase of control)]}. An interaction index value of >1 indicates a synergistic interaction between the antioxidants, a value=1 indicates additive effect and a value <1 indicates antagonistic interaction between the antioxidants.

Statistical Analysis:

Results are presented as means and standard deviations of analyses conducted in triplicate. Oxidation lag phases were defined as the first data point statistically greater than day zero within each treatment tested using one-way analysis of variance (ANOVA) with comparison of the oxidation measurement means performed using Tukey's HSD post hoc test (p=0.05). Calculations were performed using Minitab version 18 (State College, Pa., USA).

TABLE 3

Droplet size and zeta potential of 1% SSO emulsions stabilized using TWEEN 20 or bovine serum albumin (BSA) containing phosphatidylethanolamine (PE), phosphatidylserine (PS) and/or various tocopherols. Each value represents the mean (n = 3) ± standard deviations. Different letters within a column (a, b, c) are statistically different means (Turkey's test P ≤ 0.05).

| Sample | Droplet size (nm) | Droplet charge (mV) |
|---|---|---|
| TWEEN 20 | | |
| Control | 210.7 ± 7.2 a | −8.42 ± 0.39 a |
| PE | 202.7 ± 2.0 a | −8.50 ± 0.58 a |
| PS | 208.2 ± 1.7 a | −12.27 ± 0.61 b |
| α-tocopherol | 203.8 ± 3.4 a | −7.74 ± 0.38 a |
| δ-tocopherol | 222.0 ± 1.3 a | −8.25 ± 0.06 a |
| Mixed tocopherol | 203.9 ± 1.2 a | −8.50 ± 0.58 a |
| α-tocopherol + PE | 197.3 ± 1.1 a | −7.69 ± 0.31 a |
| α-tocopherol + PS | 200.3 ± 3.7 a | −9.93 ± 0.18 c |
| δ-tocopherol + PE | 222.0 ± 2.5 a | −8.79 ± 0.22 a |
| δ-tocopherol + PS | 225.6 ± 3.5 a | −11.01 ± 1.10 ab |
| Mixed tocopherol + PE | 204.0 ± 1.0 a | −9.40 ± 1.41 a |
| Mixed tocopherol + PS | 211.8 ± 3.8 a | −10.60 ± 0.63 a |
| BSA | | |
| Control | 223.9 ± 11.1 a | −33.3 ± 1.2 a |
| PE | 209.5 ± 9.3 a | −33.3 ± 0.3 a |
| PS | 235.0 ± 3.0 a | −33.8 ± 0.8 a |
| α-tocopherol | 212.8 ± 4.6 a | −32.9 ± 0.9 a |
| δ-tocopherol | 233.4 ± 10.6 a | −33.5 ± 0.9 a |
| Mixed tocopherol | 224.1 ± 16.0 a | −36.0 ± 1.0 a |
| α-tocopherol + PE | 207.8 ± 4.5 a | −32.8 ± 0.1 a |
| α-tocopherol + PS | 206.7 ± 5.3 a | −34.0 ± 0.8 a |
| δ-tocopherol + PE | 235.2 ± 8.6 a | −33.0 ± 0.4 a |
| δ-tocopherol + PS | 234.9 ± 8.6 a | −34.7 ± 0.5 a |
| Mixed tocopherol + PE | 221.0 ± 2.4 a | −34.1 ± 0.5 a |
| Mixed tocopherol + PS | 219.7 ± 9.1 a | −36.2 ± 0.7 a |

Table 3. shows the droplet size and charge for all emulsions studied. Overall, droplet size did not vary among treatments. In the TWEEN 20 emulsions, PS containing emulsions tended to be more negative than the rest of the emulsions. Emulsion droplet size did not increase during the entire storage studies. Since there were no major changes in zeta potential and particle size, these factors should not have a major impact on lipid oxidation rates between treatments PS could change the droplet charge significantly as compared to the control indicating that PS was present at the interface.

Impact PE and PS with or without Tocopherols on the Oxidation of TWEEN 20-Stabilized SSO O/W Emulsions:

The TWEEN 20-stabilized SSO emulsion had a lag phase for lipid hydroperoxides formation of 0 days and the lag phase of hexanal formation was 1 day. Addition of 3.0 μmol α-tocopherol/kg emulsion extended the hydroperoxide lag phase to 1 day and hexanal lag phase to 2 days. PE and PS did not affect the hydroperoxide and hexanal lag phase by themselves as compared to control. When PE was added with α-tocopherol in the emulsion it resulted in a hydroperoxide lag phase of 1 day and hexanal lag phase was 2 days, indicating that PE had little to no impact on the antioxidant activity of α-tocopherol. However, the combination of PS and α-tocopherol extended hydroperoxide lag phase to 5 days and hexanal lag phases to 6 days. The interaction index for PS and α-tocopherol was 5 for both hydroperoxides and hexanal indicating synergism. Synergism exhibited between PS and α-tocopherol could be due to more PS present at the interface as compared to PE, promoting greater interactions between α-tocopherol and PS.

δ-Tocopherol differs from α-tocopherol in that it has only one methyl group compared to 3 for α-tocopherol meaning that δ-tocopherol is more polar and surface active. Addition of δ-tocopherol (3.0 μmol/kg emulsion) to the Tween 20 stabilized emulsions extended the hydroperoxide lag phase to 3 days and hexanal lag phase to 4 days. PE and PS alone did not change hydroperoxide and hexanal lag phases compared to the control. When PE was added with δ-tocopherol in the emulsion the combination extended the hydroperoxide lag phase to 6 days and hexanal lag phase to 7 days. This produced an interaction index of 1.5 indicating synergism for both hydroperoxides and hexanal. The combination of PS and δ-tocopherol extended the hydroperoxide lag phase to 7 days and hexanal lag phase to 10 days resulting in an interaction index of 1.75 for hydroperoxides and 3 for hexanal. Not wishing to be bound by theory, this data suggests that synergism exhibited between PE and δ-tocopherol could be due to more δ-tocopherol at the interface as compare to α-tocopherol because of its greater surface activity. Increased surface activity of δ-tocopherol could also explain why greater synergism was observed with PS compared to α-tocopherol.

α-Tocopherol is available as a food additive but the other tocopherol homologs like δ-tocopherol are currently too expensive for use in foods. In order to take advantage of the unique properties of the other tocopherol homologs, the industry often uses mixed tocopherol, a by-product of oil refining. Addition of mixed tocopherols (3.0 μmol/kg emulsion) to the Tween 20 stabilized emulsions by themselves extended the hydroperoxide and hexanal lag phases to 3 days. PE and PS alone again did not change hydroperoxide and hexanal lag phases compared to the control. When PE was added with mixed tocopherol in the emulsion it extended both hydroperoxide and hexanal lag phases to 5 days and resulted in an interaction index of 1.67 for hydroperoxides and 1.33 for hexanal. The combination of PS and mixed tocopherol extended the hydroperoxide lag phase to 5 days and hexanal lag phase to 6 days, an interaction index of 1.25 and 3, respectively. Overall, mixed tocopherols were not as synergistic as δ-tocopherol with PE and PS. This is likely due to the mixed tocopherol having less surface active tocopherols such as α, β, and γ-tocopherols which have 2-3 methyl groups compared to the single methyl group on δ-tocopherol. This data suggests that in oil-in-water emulsions, maximum interactions between tocopherols and phospholipids are achieved with the more polar tocopherol homologs.

Impact of PE and PS with or without Tocopherols on the Oxidation of BSA Stabilized SSO O/W Emulsions:

In oil-in-water emulsions, tocopherols are primarily found in the emulsion droplet because tocopherols have essentially zero water solubility. Phospholipids could be found in the lipid droplet, at the droplet interface and suspended in structures like micelles in the continuous phase. Protein and small molecule surfactant (e.g. TWEENs)-stabilized emulsions could have different impacts on antioxidant activity by impacting the location of the tocopherol and phospholipid which in turn could impact their ability to synergistically inhibit lipid oxidation. For example, emulsifiers could impact interactions between tocopherols and phospholipids due to differences in their surface charge (−8.5 mV for TWEEN 20 vs−33 mV for BSA) which could change the location of the phospholipids through charge repulsion. In addition, proteins could form thicker emulsion droplet interfaces that could impact interactions between tocopherol in the droplet and phospholipids in the continuous phase. TWEENs are also known to form micelles in the continuous phase of emulsion that can solubilize tocopherols out of the emulsion droplet which could also impact their ability to interact with phospholipids. Due to these potential differences, synergism between tocopherols and phospholipids where also determined in BSA-stabilized oil-in-water emulsions.

The BSA-stabilized SSO emulsions had a lag phase for lipid hydroperoxides formation of 0 days and a lag phase of hexanal formation of 1 day. Addition of α-tocopherol (3.0 μmol/kg emulsion) to the emulsions extended the hydroperoxide lag phase to 3 days and increased the hexanal lag phase to 4 days. PE alone extended the hydroperoxide lag phase to 1 day and the hexanal lag phase to 4 days whereas PS alone did not affect the hydroperoxide lag phase and increased the hexanal lag phase to 4 days. When PE was added with α-tocopherol to the BSA-stabilized emulsion it extended the hydroperoxide lag phase to 4 days the hexanal lag phase to 7 days which produced interaction index of 1 for both indicating an additive effect. The combination of PS and α-tocopherol extended the hydroperoxide lag phase to 4 days and hexanal lag phase to 8 days which produced interaction indexes of 1.3 and 1.2 respectively.

Addition of δ-tocopherol (3.0 μmol/kg emulsion) to the BSA-stabilized oil-in-water emulsion extended the hydroperoxide lag phase to 4 days and hexanal lag phase to 5 days. PE alone extended the hydroperoxide lag phase to 1 day and the hexanal lag phase to 3 days and PS alone extended the hydroperoxide lag phase to 1 day and hexanal lag phases to 2 days. When PE was added with δ-tocopherol in the emulsion it extended the hydroperoxide lag phase to 7 days and hexanal lag phase to 11 days which produced interaction indexes of 1.4 and 1.7 respectively. The combination of PS and δ-tocopherol extended the hydroperoxide lag phase to 6 days and hexanal lag phase to 10 days which produced interaction indexes of 1.2 and 1.8 respectively.

Addition of 3.0 μmol mixed tocopherol/kg emulsion extended both the lag phases to 3 days. PE alone extended the hydroperoxide lag phase to 1 day and the hexanal lag phase to 3 days whereas PS alone extended the hydroperoxide lag phase to 1 day and hexanal lag phases to 2 days. When PE was added with mixed tocopherol in the emulsion it extended the hydroperoxide lag phase to 5 days and the hexanal lag phase to 7 days which produced interaction indexes of 1.3 and 1.5 respectively. The combination of PS and mixed tocopherol extended the hydroperoxide lag phase to 4 days and the hexanal lag phase to 5 days which produced interaction indexes of 1.3 and 2.5 respectively.

Table 4. contains the interaction index between tocopherols and PE or PS in 1% stripped soybean oil-in-water emulsions stabilized with either TWEEN 20 or bovine serum albumin (BSA).

TABLE 4

| | interaction index | | | |
| --- | --- | --- | --- | --- |
| | Tween 20 | | BSA | |
| sample | hydroperoxide | hexanal | hydroperoxide | hexanal |
| α-tocopherol + PE | 1 (additive) | 1 (additive) | 1 (additive) | 1 (additive) |
| α-tocopherol + PS | 5 (synergistic) | 5 (synergistic) | 1.33 (synergistic) | 1.17 (synergistic) |
| δ-tocopherol + PE | 1.5 (synergistic) | 1.5 (synergistic) | 1.4 (synergistic) | 1.67 (synergistic) |
| δ-tocopherol + PS | 1.75 (synergistic) | 3 (synergistic) | 1.2 (synergistic) | 1.8 (synergistic) |
| mixed tocopherol + PE | 1.67 (synergistic) | 1.33 (synergistic) | 1.25 (synergistic) | 1.5 (synergistic) |
| mixed tocopherol + PS | 1.25 (synergistic) | 3 (synergistic) | 1.33 (synergistic) | 2.5 (synergistic) |

In view of the above data, modified lecithin having enhanced levels of phosphatidylserine can substantially increase the oxidative stability of oil-in-water emulsions. The results show that the combination of tocopherols and PE or PS produce synergistic antioxidant activity in oil-in-water emulsions. Antioxidant combinations were able to increase the lag phase of lipid oxidation from 1.3 to 2.75 fold.

In oil-in-water emulsions, nonpolar antioxidants are more effective as defined in the antioxidant polar paradox hypothesis. More recently, the best antioxidants in oil-in-water emulsions are thought to be not only nonpolar and retained in the emulsions droplet but also surface active so they partition at the oil-water interface where lipid oxidation is most prevalent. Tocopherol homologs are nonpolar and have no water solubility. The tocopherol homologs vary in surface activity with δ-tocopherol being more surface active than α-tocopherol. It has been reported previously that the more surface active tocopherols were more effective in oil-in-water emulsions. Inhibition of lipid oxidation in this study reflects the hypothesis that the most surface active tocopherols are most effective in oil-in-water emulsions. When the tocopherols were added to the emulsion by themselves, antioxidant activity was in the order of δ≥mixed tocopherols >α. The mixed tocopherols contained only 8.5% α-tocopherol making it more surface active than α-tocopherol alone which could explain its higher antioxidant activity. Mixed tocopherols were less surface active than δ-tocopherol but two had similar antioxidant activities with δ-tocopherol being slightly better. Mixed tocopherols have been postulated to be better antioxidants than individual tocopherols because the mixtures can partition into multiple locations thus placing more antioxidant near sites of free radical generation. This could be why δ-tocopherol was not a dramatically better antioxidant than the mixed tocopherols.

Overall, the best antioxidant activity was observed with combinations of the most surface active tocopherols and phospholipids. For example, δ-tocopherol produced longer lag phases for both hydroperoxide and hexanal formation than α-tocopherol and the mixed tocopherols in the presence of both PE and PS. The phospholipids are surface active and this was observed in the reduction of zeta potential by PS in the Tween 20-stabilized oil-in-water emulsion. Not wishing to be bound by theory, the ability of PS but not PE to decrease zeta potential in the Tween emulsions could be due to the great negative charge of PS compared to PE as seen in lipid vesicles and the greater negative charge of PS compared to Tween 20 in oil-in-water emulsions at pH 7.0. PS did not change surface charge in the protein stabilized emulsions. This does not necessary mean that it was not able to concentrate at the surface of the BSA-stabilized emulsions since the BSA and PS could have similar negative charges at pH 7.0.

The combination of phospholipids and tocopherols resulted in synergistic antioxidant activity (interaction index >1.0) with the exception of α-tocopherol and PE. Again, the most surface active tocopherol were the most effective when used in combination with PE and PS. This suggests that the phospholipids and tocopherol combinations were most effective when both concentrated at the emulsion droplet interface. Conversely, the inability of α-tocopherol to produce synergistic activity could be due to its lower surface activity and thus less interactions with phospholipids.

Synergistic activity between PS and the tocopherols was greater in the TWEEN-stabilized emulsions than PE and tocopherols whereas both had a similar activity in the BSA-stabilized emulsions. This again could be due to differences in interfacial concentrations. PS is more negatively charged than PE. Since BSA is also negatively charged at pH 7.0, it's possible that charge repulsion could decrease the concentration of PS at the interface decreasing its ability to interact with tocopherols.

Not wishing to be bound by theory, the synergistic activity between the phospholipids and tocopherols could be due to several factors. Phospholipids have been reported to inhibit lipid oxidation by metal chelation. Chelators can decrease the ability of transition metals to decompose lipid hydroperoxide into free radicals. Decreased production of free radicals will decrease tocopherol degradation meaning that it can be an effective antioxidant for longer periods of time. PE and PS can also convert the oxidized form of tocopherols, the quinone, back to tocopherol regenerating tocopherols back to their active state. Regeneration of α-tocopherol by PE resulted in synergistic antioxidant in bulk oil. The observation that the synergistic activity of tocopherols and PE and PS combinations was greater with the most surface active tocopherols (e.g. δ-tocopherol and mixed tocopherols) suggests that when both were at the interface, more tocopherol regeneration occurred. While it is difficult to know the exact reasons for the observed synergistic activity, the results of this work suggest that regeneration is involved.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range. "Or" means "and/or." "Combination" is inclusive of blends, mixtures, alloys, reaction products, and the like.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A method of inhibiting or delaying lipid oxidation in a lipid-containing composition, comprising:
conducting an enzymatic conversion of a naturally derived lecithin with phospholipase D in the presence of ethanolamine, serine, or a combination thereof to form a modified lecithin comprising an enhanced level phosphatidylethanolamine, phosphatidylserine, or a combination thereof;
incorporating an effective amount of the modified lecithin into a lipid-containing composition, wherein the modified lecithin is incorporated in an amount to provide about 1000 μmol of phosphatidylethanolamine, phosphatidylserine, or a combination thereof present in the modified lecithin/kg of lipid-containing composition; and optionally further incorporating an effective amount of an additional lipid soluble antioxidant into the lipid-containing composition;

wherein the modified lecithin comprises greater than 60 wt % of phosphatidylethanolamine, phosphatidylserine, or a combination thereof based on the total weight of phospholipids present in the modified lecithin.

2. The method of claim 1, wherein the lipid-containing composition further comprises an additional lipid soluble antioxidant in an amount of about 1 to about 4000 µmol of the additional lipid soluble antioxidant/kg of lipid-containing composition, wherein the amount of additional lipid soluble antioxidant incorporated into the lipid-containing composition does not take into account the presence of endogenous tocopherols that may already be present in the lipid-containing composition.

3. The method of claim 1, wherein the additional lipid soluble antioxidant is a tocotrienol homolog, a tocopherol, or a combination thereof.

4. The method of claim 1, wherein the lipid-containing composition is an edible product, a dietary supplement, an infant formula, an edible oil, a personal care item, a cosmetic, or a medicinal/pharmaceutical, or an ingredient thereof.

5. The method of claim 4, wherein the lipid-containing composition is a vegetable oil, an animal-based oil, or a combination thereof.

6. The method of claim 4, wherein the lipid-containing composition is an emulsion, a lipid containing food, or a combination thereof.

7. The method of claim 6, wherein the lipid-containing composition further comprises an additional lipid soluble antioxidant that is a tocotrienol homolog, a tocopherol, or a combination thereof.

* * * * *